(12) United States Patent
Martin et al.

(10) Patent No.: US 7,576,233 B2
(45) Date of Patent: Aug. 18, 2009

(54) METHOD FOR THE PREPARATION OF HALOGENATED BENZONITRILES

(75) Inventors: Andreas Martin, Berlin (DE); Venkata Narayana Kalevaru, Hyderabad (IN); Bernhard Lücke, Berlin (DE); Dirk Van Deynse, Tessenderlo (BE); Marc Belmans, Tessenderlo (BE); Frank Boers, Tessenderlo (BE)

(73) Assignee: Tessenderlo Chemie S.A., Tessenderlo (BE)

( * ) Notice: Subject to any disclaimer, the term of this patent is extended or adjusted under 35 U.S.C. 154(b) by 600 days.

(21) Appl. No.: 10/516,958

(22) PCT Filed: Jun. 3, 2003

(86) PCT No.: PCT/EP03/05799

§ 371 (c)(1),
(2), (4) Date: Jan. 11, 2005

(87) PCT Pub. No.: WO03/101939

PCT Pub. Date: Dec. 11, 2003

(65) Prior Publication Data

US 2005/0176984 A1    Aug. 11, 2005

(30) Foreign Application Priority Data

Jun. 4, 2002    (EP) .................................. 02447110

(51) Int. Cl.
*C07C 255/51* (2006.01)
(52) U.S. Cl. ...................................... 558/425
(58) Field of Classification Search ................ 558/425
See application file for complete search history.

(56) References Cited

U.S. PATENT DOCUMENTS 4,147,661 A    4/1979    Higgins et al.

6,710,011 B2 *  3/2004    Mamedov et al. ........... 502/353

FOREIGN PATENT DOCUMENTS

| EP | 0 141 228 | 5/1985 |
|----|-----------|--------|
| JP | 03 044362 A | 2/1991 |

OTHER PUBLICATIONS

Huang et al., Ammoxidation of 2, 6-dichlorotoluene On Silica Supported Vanadium-Phosphorus Oxide Catalyst, Chinese Journal Of Catalysis, vol. 20 No. 6, Nov. 1999.*
Qiong, et al. "A Direct Synthesis of Aromatic Nitriles from Methylaromatic Compounds by Ammoxidation on DC-108 Catalyst," *Synthetic Communications*, vol. 29, No. 13, pp. 2349-2353, 1999.
Qiong, et al. "Catalysts for Preparing 2,6-Dichlorobenzonitrile by Ammonia Oxidation Process," Chemical Abstracts, vol. 132, No. 6, Feb. 7, 2000, Abstract No. 65726e.
Diao, et al. "Synthesis of 2,6-Dichlorobenzonitrile by Catalytic Ammoxidation," *Hebei Keji Daxue Zuebao Bianjibu*, vol. 21, No. 2, pp. 4-8, 2000, Abstract.
International Search Report completed Nov. 13, 2003 and issued to a related foreign application.

* cited by examiner

*Primary Examiner*—James O Wilson
*Assistant Examiner*—Ebenezer Sackey
(74) *Attorney, Agent, or Firm*—Knobbe, Martens, Olson & Bear, LLP

(57) ABSTRACT

The present invention relates to a method for preparing halogenated benzonitriles by vapor phase ammoxidation at a reaction temperature in the range of 300 to 500° C. in a fixed bed reactor using a three-component catalyst. More particularly, the method of the invention relates to a method for preparing 2,6-dichlorobenzonitrile (2,6-DCBN) from 2,6-dichlorotoluene (2,6-DCT) by vapor phase ammoxidation. The invention also relates to a three-component catalyst provided on a carrier and its use in a vapor phase ammoxidation reaction according to the invention. In addition, the invention provides a method for preparing the three-component catalyst.

16 Claims, No Drawings

METHOD FOR THE PREPARATION OF HALOGENATED BENZONITRILES

RELATED APPLICATIONS

This application is the U.S. National Phase under 35 U.S.C. § 371 of International Application PCT/EP03/05799, filed Jun. 3, 2003, which claims priority of EP 02447110.4, filed Jun. 4, 2002.

FIELD OF THE INVENTION

In a first aspect, the present invention relates to a method for the preparation of halogenated benzonitriles by vapour phase ammoxidation. More particularly, the method of the invention relates to a method for preparing 2,6-dichlorobenzonitrile (2,6-DCBN) from 2,6-dichlorotoluene (2,6-DCT) by vapour phase ammoxidation. In a second aspect, the present invention relates to a three-component catalyst and its use in a vapour phase ammoxidation reaction according to the invention. In a third aspect, the present invention relates to a method for preparing a three-component catalyst.

BACKGROUND OF THE INVENTION

Vapour phase ammoxidation has become an important technology. The vapour phase ammoxidation technique is a highly advantageous and a very simple method of producing nitriles in a single step and bears many superior qualities like high purity of the product, higher yields, low cost, continuous process and almost no environmental pollution. The vapour phase ammoxidation technique involves the usage of ammonia and air to convert an active methyl moiety into a cyano moiety in one step using a catalyst. This type of technique can for instance be used to prepare benzonitriles, the compounds that are derived from benzene derivates in which a methyl moiety is converted into a cyano moiety.

Halogenated benzonitriles consists of benzonitriles, which bear one or more halogen atoms, such as fluorine, chlorine, bromine or iodine. A particular example is 2,6-dichlorobenzonitrile (2,6-DCBN). In the recent years, there has been an increasing demand for 2,6-dichlorobenzonitrile (2,6-DCBN) due to its wide use in the chemical industry. It is an effective weed killer per se. Once 2,6-DCBN is used as weedicide, it is expected to be effective for a long period of time and prevents the growth of weeds even for many years. In addition, the toxic effects of 2,6-DCBN towards mammals are reported to be very low. 2,6-DCBN is also an important intermediate for agricultural chemicals and medicines. Many agricultural chemicals such as flufenoxuron, flucycloxuron, hexaflumuron, chlorfluazurin, diflubenzuron, teflubenzuron etc. can be prepared from 2,6-DCBN. 2,6-DCBN is also a starting material for preparing insecticides. In addition, 2,6-DCBN is also used to prepare polyphenyl ether hydrocyanic ester, which is one of the best kinds of special engineering plastics with the most outstanding features in today's world.

The preparation of halogenated benzonitriles in general is a very challenging task. Because of the presence of halogen atoms, the accessibility to the methyl moiety for N-insertion is restricted as a result of steric hindrance. In particular, the preparation of 2,6-dichlorobenzonitrile (2,6-DCBN) from 2,6 dichlorotoluene (DCT) is difficult as a result of the steric hindrance caused by the presence of the two bulky chlorine atoms on both the ortho positions of the methyl moiety in 2,6-DCT.

Methods to prepare 2,6-DCBN through vapour phase ammoxidation of 2,6-DCT over catalysts are known from the European patent application No. 0 273 317, which discloses the use of a multi-component catalytic system comprising Fe—Sb—V—Cr—O/$SiO_2$ for the ammoxidation of 2,6-DCT, and from U.S. Pat. No. 4,530,797, which describes a method for the ammoxidation of 2,6-DCT using VPO/$SiO_2$ as a catalyst, both carried out using fluidised bed reactors. This type of reactors shows disadvantages including a great demand on mechanical stability of a catalyst against abrasion. In addition, these documents do not describe methods whereby a high conversion of more than 99% of 2,6-DCT can be obtained. This implies that these methods still show additional separation or recycling costs. Furthermore, the described methods show many disadvantages from industrial production point of view such as low space-time yields, very high residence times and low inputs of 2,6-DCT per unit weight of the catalyst used.

Therefore, it is an object of the present invention to provide an improved vapour phase ammoxidation method, which overcomes the above-mentioned disadvantages. More in particular, the present invention provides an Improved method for obtaining 2,6-DCBN by vapour phase ammoxidation of 2,6 DCT, by a process carried out In a fixed bed reactor. Compared with known methods of 2,6-DCBN preparation by vapour phase ammoxidation, the present invention provides an improvement of several reaction parameters. Another object of the invention consists of providing higher molar yields. Yet another object of the invention is to obtain higher space-time yields. Also, the invention aims to provide higher conversion rates of 2,6-DCT.

Further, it is also an object of the Invention to provide a suitable catalyst for carrying out the vapour phase ammoxidation method. The invention also aims to provide an easy method for preparing the catalyst for use In the vapour phase ammoxidation process.

SUMMARY OF THE INVENTION

In a first embodiment, the present Invention relates to a method for the preparation of halogenated benzonitriles by vapour phase ammoxidation of halogenated $C_1$ to $C_6$ alkyl benzenes at a reaction temperature comprised in the range of 300 to 500° C., using a three-component catalyst into a fixed bed reactor wherein said catalyst consists of a promoted VPO active phase provided on a carrier. In particular, the present invention relates to a method for the preparation of 2,6-dichlorobenzonitrile by vapour phase ammoxidation of 2,6-dichlorotoluene at a reaction temperature comprised in the range of 300 to 500° C. in a fixed bed reactor, using a three-component catalyst, wherein said catalyst consists of a promoted VPO active phase provided on a carrier. This method for preparing 2,6-dichlorobenzonitrile results in an improvement of several reaction parameters compared with vapour phase ammoxidation methods known so far, including higher molar yields and higher space-time yields of 2,6-DCBN in addition to higher conversion rates of 2,6-DCT.

In a second embodiment, the present invention relates to a catalyst, suitable for use in the above-described method, comprising a VPO active phase provided on a carrier, more particularly a $V_1P_aM_bAl_cO_x$ or $V_1P_aM_bTi_cO_x$ catalyst wherein M is chosen from the group comprising Cr, Fe, Co and Mo; a is 0.1-2.0; b is 0.002-1.0; c is 2.0-10.0, and x is determined by the valences of other component elements.

In a third embodiment, the present invention relates to a method for the preparation of a three-component catalyst comprising the steps of:

preparing a bulk VPO precursor;

impregnating said bulk VPO precursor with a promoter element in order to obtain a bulk promoted VPO precursor; and adding a carrier to said bulk promoted VPO precursor in order to obtain a VPO catalyst.

This preparation method allows providing a highly active and selective catalyst whereby only negligible amounts of expected amorphous phases are formed. This novel and simple method of preparation allows obtaining a high dispersion of the active phase of the catalyst on a carrier, which leads to an improved catalyst activity.

DETAILED DESCRIPTION OF THE INVENTION

The main focus of the present invention relates to a method for preparing halogenated benzonitriles by vapour phase ammoxidation of halogenated $C_1$ to $C_6$ alkyl benzenes at a reaction temperature comprised in the range of 300 to 500° C., using a three-component catalyst into a fixed bed reactor.

"Benzonitriles" refers to the compounds that are derived from benzene derivates in which a methyl moiety is converted into a cyano moiety. With "halogenated benzonitriles" are meant benzonitriles, which bear one or more halogen moieties, such as fluorine, chlorine, bromine or iodine atoms. A particular example is 2,6-dichlorobenzonitrile (2,6-DCBN).

"Vapour phase ammoxidation" refers to the process wherein an active methyl moiety is converted Into a cyano moiety in one step using a catalyst and using gases like ammonia and air and normally in the presence of steam.

According to the method of the invention, the starting compounds are "halogenated $C_1$ to $C_6$ alkyl benzenes". The term "halogenated $C_1$ to $C_6$ alkyl benzenes" refers to benzene derivates, which bear one or more halogen atoms, such as fluorine, chlorine, bromine or iodine, and one or more alkyl moieties. The term "alkyl" moiety as used herein means a straight chain or branched-chain saturated hydrocarbon moiety containing 1 to 6 carbon atoms. Examples of suitable alkyl moieties include but are not limited to methyl, ethyl, diethyl, n-propyl, isopropyl, di-isopropyl, n-butyl, isobutyl, sec-butyl, tert-butyl, pentyl, hexyl, and the like.

In particular, di- or tri-halogenated $C_1$ to $C_6$ alkyl benzenes are preferred. For instance, di- or tri-halogenated toluene may be used to prepare halogenated benzonitriles. According to the method of the invention, toluene derivatives having chlorine atoms at the 2,6-position such as 2,6-dichlorotoluene, 2,3,6-trichlorotoluene and 2,4,6-trichlorotoluene, may for example be used to prepare 2,6-dichlorobenzonitrile, 2,3,6-trichlorobenzonitrile and 2,4,6-trichlorobenzonitrile, respectively. Likewise, toluene derivatives having chlorine atoms at the 2,4-position or 3,4-position, such as 2,4-dichlorotoluene and 3,4-dichlorotoluene, respectively, may be used according to the method of the invention to prepare 2,4-dichlorobenzonitrile and 3,4-dichlorobenzonitrile, respectively.

In a preferred embodiment, the invention relates to a method wherein said halogenated $C_1$ to $C_6$ alkyl benzene is di-halogenated toluene. "Di-halogenated toluene" as used herein refers to methylbenzene, which has two halogen atoms such as fluorine, chlorine, bromine or iodine atoms; preferably with two similar halogen atoms and more preferably, the di-halogenated toluene is di-chlorinated toluene.

In an even more preferred embodiment, the said di-halogenated toluene is 2,6-dichlorotoluene. Thus, the invention relates to a method for preparing 2,6-dichlorobenzonitrile by vapour phase ammoxidation of 2,6-dichlorotoluene in a fixed bed reactor, using a three-component catalyst.

A "fixed bed reactor" is defined as a reactor provided with a fixed bed wherein a solid catalyst is applied. A catalyst is a substance that increases the rate of a chemical reaction without being consumed in the reaction. The "VPO catalyst" as used herein, refers to a catalyst wherein the catalyst consists of three components, i.e. vanadium (V), phosphorus (P) and oxide (O). The VPO catalyst as used herein refers to the "three-component catalyst".

The method according to the invention is carried out at particular reaction conditions. In a preferred embodiment, the method of the present invention is carried out at a reaction temperature comprised in the range of 350 to 450° C. The optimum temperature depends on the several factors such as the concentration of the organic feed, the amount of catalyst used, feed gas composition and the contact time.

An object of the present method involves reducing the contact time, in order to avoid over-oxidation. In another embodiment, the invention provides for a method wherein the residence time is less than 10 seconds, preferably less than 8 seconds. The "residence time" or "contact time" are used herein as synonyms and refer to the time reagents are in contact with the catalyst particles in said reactor. In the present invention the contact time is calculated at STP, i.e. standard temperature and pressure. The residence time is defined as the reciprocal of space velocity and the unit is seconds.

According to the invention, air, $NH_3$ and $N_2$ are supplied to a fixed bed reactor comprising a three-component catalyst. The organic feed, in particular 2,6-DCT and water are injected in said reactor and vapourised in a preheating zone provided on the top of the catalyst bed. Furthermore, the invention provides for a method wherein the molar concentration of 2,6-DCT is in the range between 0.6 to 5% and the ratio of $O/NH_3$ is In the range between 0.5 to 4.0 moles. The mole ratio of $NH_3$ to 2,6-DCT is in the range of 1 to 15, preferably 2 to 10. The mole ratio of air to 2,6-DCT is less than 80 moles, preferably less than 50 moles.

Ammoxidation is considered to be the most promising and potential technique for the production of the nitriles from their corresponding hydrocarbons. The ammoxidation of 2,6-DCT to 2,6-DCBN is indeed a very challenging task and needs most outstanding efforts to obtain high conversion with higher yield of 2,6-DCBN. Because the methyl moiety to be ammoxidised in 2,6-DCT is less active than that in other conventional alkyl aromatic hydrocarbons and hetero aromatic hydrocarbons. The accessibility to the methyl moiety for N-insertion is restricted to a greater extent due to steric hindrance, because of the presence of the two bulky chlorine atoms on both the ortho positions of the methyl moiety in 2,6-DCT. The present invention provides a method, which improves both the molar yields and space-time yields for the preparation of 2,6-DCBN to a maximum extent for economical industrial production. The invention provides a method for the preparation of 2,6-DCBN from a highly steric hindered 2,6-DCT molecule under suitable reaction conditions by vapour phase ammoxidation using cheaply available reactants like air, $NH_3$ and $H_2O$ in addition to 2,6-DCT.

The method according to the present invention for preparing 2,6-DCBN from 2,6-DCT by vapour phase ammoxidation can be carried out using VPO based catalysts In a fixed bed tubular quartz reactor at elevated temperatures of 300 to 500° C. under normal atmospheric pressure.

The supply of nitrogen gas as a dilution gas aims to maintain constant space velocity during optimization of the process parameters and also to increase gas hourly space velocity (GHSV), or in other words to reduce residence times. The "space velocity" of a gas refers to the volume of a gas measured at a specific temperature and pressure passing through the catalyst bed in a unit time. The "gas hourly space velocity (GHSV)" is defined as the total volume of a gas measured at a specific temperature and pressure passing through the catalyst bed per unit time (one hour). $H_2O$ is normally added in the form of a liquid at room temperature which will be converted in the form of water vapour or steam in the preheating zone provided on the top of the catalyst bed, whereby the latter is added to the feed gas in a fixed proportion.

The method of the present Invention provides several important advantages compared to methods reported so far in the literature. One advantage includes the possibility of preparing 2,6-DCBN in greater yields, i.e. at least 85.8 mol % yield with almost total conversion of 2,6-DCT, i.e. more than 99%. The method provides higher gas hourly space velocities (GHSV) and lower residence times. The GHSV is preferably comprised in the range from 600 to 2400 $h^{-1}$ and the residence times comprises between 1.5 to 6.0 seconds. Further, the method allows preparing 2,6-DCBN at better and higher space-time-yields (STY) which are comprised in the range from 100-150 g/kg.cat/h. The "space-time yield (STY)" is defined herein as the quantity of product (2,6-DCBN) obtained per kg of catalyst per unit time (in one hour). To our knowledge, the STY claimed in the present invention, is the highest compared to all other processes reported so far in the literature regardless of the catalyst system used. In addition, the major end product of the method according to the invention is 2,6-DCBN. Only small amounts of total oxidation products, i.e. CO and $CO_2$, are produced. The formation of certain amounts of $NH_4Cl$, as a by-product, is also observed, but is negligible. Thus, the method provides end product of DCBN in higher yield with high purity.

In another embodiment, the invention relates to a method wherein said catalyst comprises a VPO active phase provided on a carrier. "A carrier" or "a support" is used herein as synonyms. The loading of VPO phase on a carrier can vary in the range from 5-50 wt %, and more preferably in the range from 10 to 30 wt %. The use of a carrier provides many advantages including lowering the VPO catalyst concentration, increasing the strength of the catalyst, providing high dispersion of the active phase, providing good thermal stability, reducing the reaction temperature and also enhancing the life of the catalyst and thus increasing the economy of the process. Suitable carriers may include. alumina, titania, silica, beryllia, zirconia, magnesia, silicon carbide, asbestos, or diatomaceous earth. In a preferred embodiment, said VPO active phase of the catalyst is provided on an $Al_2O_3$ carrier, and more preferably on a $\gamma$-$Al_2O_3$ carrier. Alternatively, the VPO active phase is provided on a $TiO_2$ carrier. More preferred, said $TiO_2$ carrier consists of the anatase phase.

The catalyst comprises a promoter element. "Promoter elements" are substances, which are added to catalysts in order to improve their catalytic activity and selectivity. Suitable promoter elements may include calcium, natrium, barium, manganese, nickel, chromium, tin, magnesium, iron, cobalt or molybdenum. More preferably, the promoter elements used for the VPO catalyst are selected from the group comprising Cr, Fe, Co and Mo. In an even more preferred embodiment, the invention provides a method wherein said catalyst comprises a $V_1P_aM_bAl_cO_x$ or $V_1P_aM_bTi_cO_x$ catalyst wherein M is chosen from the group comprising Cr, Fe, Co and Mo; a is 0.1-2.0; b is 0.002-1.0; c is 2.0-10.0, and x is determined by the valences of other component elements.

The active catalyst used in the method of the invention contains mainly two phases under working conditions: a $(VO)_2P_2O_7$ phase and a $(NH_4)_2(VO)_3(P_2O_7)_2$ phase. This decomposition of the catalyst into two phases during operational conditions is an important feature, as it does not lead to decrease in both catalytic activity and selectivity but conversely improves the catalytic activity. A synergistic activity between these two phases can be responsible for higher activity and selectivity of the catalysts. Besides these phases also some micro domains of $V^{+5}$ phases, i.e. amorphous proportions, may be present on the surface of the catalyst.

Another embodiment of the invention concerns the addition of halogenated alkanes to said reactor during the ammoxidation reaction. "Halogenated alkanes" are defined as aliphatic or aromatic unsaturated hydrocarbons, which are substituted with one or more halogen atoms, such as fluorine, chlorine, bromine or iodine. A preferred group of halogenated alkanes which may be added to said reactor include bromide containing alkanes, such as for instance methyl bromide, ethyl bromide, dibromomethane, carbon tetra bromide, n-propyl-bromide, i-propyl-bromide, n-butyl-bromide, 1-butyl-bromide, sec-butyl-bromide, i-amyl-bromide, sec-amyl-bromide, tert-amyl-bromide, cyclopentyl bromide, cyclohexyl bromide and the like. In a preferred embodiment of the method of the invention comprises the step of supplying ethyl bromide to said reactor. More particularly, according to the method of the Invention, ethyl bromide may be added in the range from 0.5 to 5 vol %, preferably in the range from 1 to 3 vol % of 2,6-DCT feed.

As mentioned above, ethyl bromide and water vapour may be added to the feed gas. Addition of ethyl bromide in the range of 0.5 to 5 vol %, preferably in the range of 1 to 3 vol % of 2,6-DCT feed has a promotional effect on the catalytic performance of almost all the catalysts of the present invention. Furthermore, the combination of both the water vapour and ethyl bromide in the feed gas may influence the efficiency of certain catalysts, as illustrated in examples 6 and 12. For example, the addition of steam in the feed gas in a fixed proportion has a beneficial effect on the catalytic performance of a VPCrO/$TiO_2$ catalyst (see also Tables 3 and 4), while the addition of water vapour has no considerable effect in the presence of ethyl bromide in the reactant feed gas on the catalytic performance of this Cr promoted catalyst. The addition of both water vapour and ethyl bromide admixture in the reactant feed gas has a detrimental effect especially on the catalytic performance of Co and Fe promoted catalysts, i.e. VPCoO/$\gamma$-$Al_2O_3$ and VPFeO/$\gamma$-$Al_2O_3$ catalysts. When adding ethyl bromide, in the absence of water vapour, both catalysts remarkably displayed a better catalytic performance exhibiting DCBN yields of 89.5% and 86.6% respectively (see also Table 4).

In particular, the VPCoO/$\gamma$-$Al_2O_3$ catalyst shows a remarkable potentiality and exhibits a conversion of 2,6-DCT, as high as ~100% with 85.8% molar yield and 130-140 g/kg cat/h space-time yields of 2,6-DCBN, in absence of ethyl bromide admixture, while in presence of ethyl bromide admixture, a maximum DCBN yield of 89.5 mol %, space-time yields of 141 g/kg cat/h at almost total conversion was also successfully achieved over this VPCoO/$\gamma$-$Al_2O_3$ catalyst. Therefore, in a particularly preferred embodiment, the invention relates to a method, wherein said catalyst is a VPCoO catalyst provided on the $\gamma$-$Al_2O_3$ carrier.

The Invention provides a method wherein the dilution of organic substrate (2,6-DCT) with water is less than 40 moles, preferably less than 25 moles per each mole of 2,6-DCT fed. $H_2O$ is generally added in the form of a liquid at room temperature but will be converted into vapour or steam in the preheating zone, whereby the after is mixed with the feed gas in a fixed proportion. The presence of water vapour plays an important role in controlling the surface metal oxide structures. Moisture is able to interact with oxygen functionalities of the surface vanadia species via hydrogen-bonding. The presence of water vapour is expected to suppress the formation of total oxidation products by blocking the most active sites on vanadium oxide structures. Addition of water vapour also moderates the temperature variation in the reactor which provide thermal ballast. The presence of water vapour is also considered to help the easy desorption of products and also limit the adsorption of reactants due to competitive adsorption. In the presence of steam the coordination characteristics of active centres and the surface acid-base properties are believed to be modified. In general, the partial pressure of steam, is expected to affect i) the ratio of Bronsted to Lewis acid sites, ii) hydrolytic break of V—O—P and P—O—P bonds, iii) the degree of surface hydroxylation and so on. Also, mixing of steam with organic feed can significantly enhance the selectivity of desired product. But too much dilution is also found to be not suitable for obtaining higher yields of 2,6-DCBN.

In another embodiment, the invention provides for a method wherein whereby the catalyst is diluted with an inert medium in the ratio of 0.5 to 2.0 by weight with respect to the weight of said catalyst prior to its loading in the reactor. Since the ammoxidation reaction is exothermic in nature, dilution of the catalyst with an inert medium like porcelain beads, corundum ($Al_2O_3$) particles, quartz beads, glass beads, or the like, is recommended in the ratio of 1:2, preferably 1:1 by weight.

The method according to the invention can be carried out in a fixed bed tubular quartz reactor, for instance of 16 mm I.d. and 25 mm long, and heated in an electrical furnace. Air, $NH_3$ and $N_2$ supplied are commercially available gases from compressed gas cylinders. The organic feed, i.e. 2,6-DCT, and the water are injected by means of high precision HPLC pumps and vapourised in a preheating zone provided on the top of the catalyst bed. Five grams of catalyst particles mixed with corundum crystals in a 1:1 dilution by weight may be loaded in the reactor and the reaction is performed. The obtained product stream can be collected every half-an hour and analysed by gas chromatography. The product mixture can easily be trapped by condensing in an ice-cooled solvent such as ethanol, acetone, ether, chloroform, dichloromethane or any other suitable solvent. In order to assure that there is no escape of any organic vapour, collection of the product stream In 2 to 3 series of ice cooled traps with any one of the above-mentioned solvents is recommended. The $1^{st}$ trap is maintained at −15° C. (ice+salt) and the $2^{nd}$ trap at −10° C., and so on. The total oxidation products can be continuously monitored on line using a non-dispersive infrared analyser.

In another embodiment, the Invention relates to a catalyst consisting of a VPO active phase provided on a carrier suitable for use in the ammoxidation method according to the invention. The VPO active phase consists mainly of the three elements vanadium, phosphorus and oxygen. Suitable promoter elements, which improve the catalytic activity and selectivity include calcium, natrium, barium, manganese, nickel, chromium, tin, magnesium, iron, cobalt or molybdenum etc. More preferably, the promoter elements of the VPO catalyst are selected from the group comprising Cr, Fe, Co and Mo. Suitable carriers may include alumina, titania, silica, beryllia, zirconia, magnesia, silicon carbide, asbestos, or diatomaceous earth. The catalyst according to the invention comprises a $V_1P_aM_bAl_cO_x$ or $V_1P_aM_bTi_cO_x$ catalyst wherein M is chosen from the group comprising Cr, Fe, Co and Mo; a is 0.1-2.0; b is 0.002-1.0; c is 2.0-10.0, and x is determined by the valences of other component elements. In a preferred embodiment, said VPO active phase of the catalyst is provided on an $Al_1O_3$ carrier, and more preferably on a $\gamma$-$Al_2O_3$ carrier. Alternatively, the VPO active phase is provided on a $TiO_2$ carrier. More preferred, said $TiO_2$ carrier consists of the anatase phase. The carrier provides high surface area compared to bulk catalyst, high dispersion for the active promoted VPO and good thermal stability to the catalyst. In addition, i provides good pellet strength and long life to the catalyst.

In contrast to most other known catalysts, which comprise multi-component and more complex catalyst compositions consisting of two or more promoters with them, the catalyst of the present invention comprises three components and represents a very simple system exhibiting better performance. The three components consist of vanadium (V), phosphorus (P) and oxide (O). In addition, due to a high dispersion of the active phase of the catalyst on the carrier, a catalyst having a high activity and selectivity is obtained. The invention thus provides a three-component catalyst which catalyses the preparation of 2,6-DCBN by ammonia oxidation of 2,6-DCT through a single step, which has a high reactivity and selectivity, and a long lasting valid time.

In yet another embodiment, the invention provides a method for preparing a catalyst, comprising the steps of:
  preparing a bulk VPO precursor;
  impregnating said bulk VPO precursor with a promoter element in order to obtain a bulk promoted VPO precursor; and
  adding a carrier to said bulk promoted VPO precursor in order to obtain a VPO catalyst.

The invention provides a very simple method for preparing highly active and selective supported VPO catalysts. As used herein, the term "bulk VPO catalyst", "bulk VPO precursor", or the like, refers to an active phase consisting of three elements, vanadium, phosphorus and oxygen, which is not been provided on a carrier. The term "bulk promoted VPO catalyst", "bulk promoted VPO precursor" or the like, refer to a VPO active phase not deposited on a carrier, but provided with a promoter element. The term "supported and promoted VPO catalyst" or "VPO catalyst" or the like, define a VPO active phase provided with a promoter element and deposited on a carrier.

The present invention provides a simple method for preparation of three-component catalysts in contrast to earlier cumbersome processes involving multi-component catalytic systems. The process for the preparation of a catalyst according to the present invention involves three steps. The first step involves the preparation of vanadyl hydrogen phosphate hemihydrate ($VOHPO_4 \cdot 0.5H_2O$) precursor through an organic medium. The second step deals with the preparation of bulk promoted VPO precursors by the impregnation of the vanadyl hydrogen phosphate hemihydrate ($VOHPO_4 \cdot 0.5H_2O$) precursor with either alcoholic or aqueous solutions of prescribed amounts of promoters. In the third step, this precursor is further used to prepare supported and promoted VPO catalysts by a very simple solid-solid wetting method. The solid-solid wetting method for preparing supported VPO catalysts is very simple and effective method to give high dispersion of active phase which In turn is responsible and crucial for higher activity and selectivity of this catalyst.

More particularly, the method for preparing a catalyst according to the invention comprises the steps of:
  refluxing of a vanadium source in the presence of alcohols to obtain a solution containing reduced vanadium species;
  adding of a phosphorus source and refluxing said solution in order to obtain a bulk VPO precursor;

impregnation of said bulk VPO precursor with an alcoholic or aqueous solution of a promoter element to obtain a bulk promoted VPO precursor;

mixing said bulk promoted VPO precursor with a carrier powder; and shaping and calcining the resultant mixture to obtain a supported and promoted VPO catalyst.

The preparation of the $VOHPO_4*0.5H_2O$ precursor involves refluxing of vanadium rich compounds. These vanadium rich compounds may include ammonium metavanadate, vanadyl sulphate, vanadyl acetyl acetonate, vanadyl oxalate, vanadyl phosphate, vanadium-containing heteropoly acid, salts of the same or the like. Also, an aqueous hydrogen peroxide solution of vanadium oxide or vanadic acid (vanadate) may be used. Preferably oxides of vanadium such as $V_2O_5$ are used in a mixture of aliphatic alcohols such as ethanol, propanol, butanol, pentanol or the like, and aromatic alcohols, such as benzyl alcohol. Subsequently, phosphorus containing molecules, such as phosphates, ammonium phosphates including ammonium dihydrogenphosphate; diammonium hydrogenphosphate or ammonium hexafluorophosphate, $P_2O_5$, meta phosphoric acid, ortho phosphoric acid, pyro phosphoric acid, or the like, are added and again refluxed for a few hours more. The resulting slurry is vacuum filtered, washed and dried at 120° C. for 24 hours. Several bulk VPO precursors can be prepared using this procedure with a variety of P/V ratio (atomic ratio) over a wide range from 0.1 to 2.0 preferably 0.5 to 1.5. In a preferred embodiment, said vanadium source is $V_2O_5$ and said phosphorous source is o—$H_3PO_4$. The preparation of said catalyst precursors through organic route additionally induces a disorderliness in the plane layer stacking of the catalyst precursor, which enhances several factors such as the catalytic activity of the catalyst.

The preparation of the catalyst according to the invention further comprises the preparation of bulk promoted VPO catalysts wherein the $VOHPO_4*0.5H_2O$ precursor in powder form is impregnated with an alcoholic or aqueous solution of a suitable promoter. Suitable promoter elements may include calcium, natrium, barium, manganese, nickel, chromium, tin, magnesium, iron, cobalt or molybdenum. In a preferred embodiment, said promoter element comprises Cr, Fe, Co or Mo.

Subsequently, the bulk promoted VPO precursor is thoroughly mixed with either a carrier, present in powder form with V/carrier ratio in the range of 1:2 to 1:10, preferably in the range of 1:6: Suitable carriers may include alumina, titania, silica, zirconia, beryllia, magnesia, silicon carbide, asbestos, or diatomaceous earth. In a preferred embodiment, the bulk promoted VPO precursor is thoroughly mixed with either an $Al_2O_3$ carrier, and more preferably on a $\gamma$-$Al_2O_3$ carrier, or a $TiO_2$ carrier. The $TiO_2$ carrier used may either be anatase or rutile or a mixture of both, possessing a BET surface area, not more than 150 $m^2$/g and preferably not more than 100 $m^2$/g.

Then, the resultant mixture is heated in a calcining atmosphere at a temperature in the range of 300° C. to 900° C., preferably in the range of 350° C. to 700° C., for a period of 2 to 6 hours. A calcining atmosphere under weak oxidising strength is preferred, which may comprise an atmosphere of 0.5% $O_2/N_2$. The calcinations under weakly oxidising atmosphere (0.5% $O_2/N_2$) permits to obtain suitable oxidation state of vanadium in the resulting final catalyst as the oxidation state of vanadium plays a key role on the catalytic performance of the final catalyst.

The method for preparing the catalyst according to the invention is particularly suitable as it allows providing for a very selective and efficient catalyst, showing particularly stable catalytic activity. For example, a fresh catalyst which contains exclusively $(VO)_2P_2O$ phase shows no decline in the catalytic activity and selectivity even if a part of it undergoes phase transformation into $(NH_4)_2(VO)_3(P_2O_7)_2$ phase under severe reaction conditions after few hours of operation. Both the phases are found to be stable and display good activity and selectivity through out the runs. In addition, no loss of phosphorus and vanadium is observed even after 100 hours of time-on-stream studies and the total contents of V and P are found to be similar in both the fresh and used catalysts as evidenced by ICP-OES analysis.

The method of the invention provides for the preparation of promoted VPO catalysts, exhibiting a much superior catalytic performance compared to bulk and supported VPO catalysts with different P/V ratios.

In another embodiment, the invention relates to the use of a catalyst according to the invention, and prepared according to the invention in a vapour phase ammoxidation reaction. More particularly, the catalyst according to the invention can be used to carry out a vapour phase ammoxidation reaction according to the invention. Thus, the catalyst according to the invention can be used in the preparation of halogenated benzonitriles by vapour phase ammoxidation of halogenated $C_1$ to $C_6$ alkyl benzenes at a reaction temperature comprised in the range of 300 to 500° C. in a fixed bed reactor. In particular, the catalyst according to the invention is used to prepare 2,6-dichlorobenzonitrile from 2,6-dichlorotoluene in a vapour phase ammoxidation reaction according to the invention.

In addition, the catalyst of the invention is not only active for the ammoxidation of alkyl aromatic hydrocarbons such as for instance alkyl benzenes, but it is also particularly suitable and equally active and selective for the ammoxidation of hetero aromatic hydrocarbons. The term "hetero aromatic hydrocarbons" refers to aromatic compounds in which one or more of the atoms in the ring is an element other than carbon, e.g. sulphur, nitrogen, etc . . . Examples of such hetero aromatic hydrocarbon include but are not limited to $\alpha$-, $\beta$- and $\gamma$-methyl pyridines, and methyl pyrazines, in particular 2-methyl pyrazine.

The present invention is illustrated in greater detail with reference to the following examples, but it is understood that the present invention is not deemed to be limited thereto. Examples 1, 2 and 3 illustrate the preparation of a VPO catalyst according to the invention. Examples 4 and 5 describe the activity and selectivity of different VPO catalysts used during an ammoxidation reaction carried out according to the invention. Example 6 refers to the influence of water vapour in the feed gas on the catalytic performance of catalysts. Examples 7 to 11 describe ammoxidation reactions carried out following particular reaction conditions according to the invention and the catalytic performances of the catalysts used. Example 12 illustrates the influence of the addition of ethyl bromide in the presence or absence of water vapour during an ammoxidation reaction. In the following examples, the conversion, yield and selectivity based on 2,6 DCT are defined as follows:

Conversion (%)=AB×100 where A is the number of moles reacted 2,6-DCT, and

B is the number of moles of 2,6-DCT fed to the reaction zone.

Yield (%)=C/D×100 where C is the number of moles 2,6-DCBN obtained, and

D is the number of moles of 2,6-DCT fed to the reaction zone.

selectivity (%)=E/F×100 where E is the number of moles 2,6-DCBN obtained, and

F is the number of moles reacted 2,6-DCT.

Space-time yield (g/kg/h)=G/H×h$^{-1}$ where G is the amount in grams of 2,6-DCBN obtained in 1 hour, and H is the amount in kilograms of catalyst used in 1 hour.

EXAMPLES

Example 1

Example 1 illustrates the preparation of bulk VPO catalysts. The VPO precursors were prepared through organic medium using alcohols as reducing agents as described below.

52.5 g of $V_2O_5$ powder was suspended in a mixture of 315 ml of 2-butanol and 210 ml of benzyl alcohol, taken in a 3-necked 1 litre round bottom flask and the suspension was stirred continuously under reflux for a period of 3 hours. The mixture was then cooled to room temperature and the stirring was continued at room temperature for over night (~20 hours) before the addition of o—$H_3PO_4$. Then an appropriate amount of 85% o—$H_3PO_4$ (the quantity of o—$H_3PO_4$ depends on the P/V ratio of the precursor) was added slowly and the resultant mixture was again heated and maintained under reflux with constant stirring for another 2 hours then the resultant slurry was cooled to room temperature, filtered and washed with ethanol for several times. The precursor obtained was oven dried at 120° C. for 24 hours. Using the similar procedure, several bulk VPO precursors were prepared with different P/V ratios over a wide range. The phase composition in all oven dried precursors was found to be $VOHPO_4 * 0.5H_2O$. The precursors were calcined at 450° C. for 3h in $N_2$ atmosphere to obtain the desired bulk catalyst which contains exclusively $(VO)_2P_2O_7$ phase.

Example 2

Example 2 Illustrates the preparation of promoted VPO catalysts.

The bulk promoted VPO catalysts were prepared by the impregnation (excess solvent method) of the bulk precursor (P/V ratio=0.95) with a solution (using either ethanol or water as solvents) containing prescribed amounts of additives (Cr, Fe, Co and Mo salts with M/V is in the range from 0.002 to 1.0 and preferably in the range from 0.01 to 0.4), removal of excess solvent by evaporation on a hot plate to dryness followed by oven drying at 120° C. for 16 h. This precursor is further used for preparing supported and promoted VPO catalysts by solid-solid wetting method using two different oxide supports such as γ-$Al_2O_3$ and $TiO_2$ (anatase).

Example 3

Example 3 illustrates the preparation of supported and promoted VPO catalysts.

The supported and promoted VPO catalysts were prepared by solid-solid wetting method using bulk promoted $VOHPO_4*0.5H_2O$ precursor (with a P/V ratio of 0.95), prepared by a method as described in examples 1 and 2. The carriers used were either γ-$Al_2O_3$ or $TiO_2$, having a BET surface area of ~100 m$^2$/g. Appropriate quantities of powders of bulk promoted VPO precursor and a carrier were mixed thoroughly and ground in an agate mortar and then transferred to a grinding machine where the two powders were electrically mixed thoroughly for –5 to 10 minutes. The resulting solid mixture was pelletised, crushed and sieved to the required particle size and then calcined at 450° C. for 3 hours in 0.5%$O_2/N_2$ atmosphere. The resultant catalyst after calcination, contains 5 to 50 wt % VPO preferably 10 to 30 wt % and the rest is support material. The phase composition in the fresh calcined catalyst Is found to be $(VO)_2P_2O_7$ in addition to support phase. The formation of certain amounts of amorphous phases/solid solutions as a result of interactions with promoter source is also expected in all the catalysts of the present study.

Example 4

Example 4 describes the activity and selectivity of a VPO catalysts on a γ-$Al_2O_3$ carrier used during an ammoxidation reaction carried out according to the invention.

Ammoxidation runs were carried out in a fixed bed tubular quartz reactor, which is filled with 5 g of catalyst particles prepared by the methods described in examples 1 to 3 and mixed with corundum particles of the same size in 1:1 by weight ratio. A preheating zone is provided on the top of the catalyst bed. The catalyst was activated in a mixture of air and $NH_3$ at 400° C. for 4 hours and then the catalytic runs were performed. The 2,6-DCT and $H_2O$ were pumped in the mole ratio of 1:15 to 20. The product stream was collected for every half-an-hour and analysed by gas chromatography.

The reaction was carried out under the following reaction conditions. A reaction temperature of 350 to 400° C. was used, and the GHSV comprised between 650-750 h$^{-1}$. The contact time consisted of 4.8 to 5.5 seconds. The mole ratio of 2,6-DCT:$H_2O$:$NH_3$:air was 1:15:3-4:21, the molar concentration of 2,6-DCT was 2.4% and the ratio of O/$NH_3$ was 1.1%. The results are shown in Table 1.

TABLE 1

Influence of promoters on the activity and selectivity behaviour of alumina supported VPO catalysts.

| Catalyst | Conversion, % (2,6-DCT) | Yield, % (2,6-DCBN) | Selectivity, % (2,6-DCBN) | STY (g/kg · cat/h) |
|---|---|---|---|---|
| VPCoO/γ-$Al_2O_3$ | 99.3 | 85.8 | 86.4 | 137.5 |
| VPFeO/γ-$Al_2O_3$ | 97.4 | 82.7 | 84.9 | 132.5 |
| VPMoO/γ-$Al_2O_3$ | 99.0 | 79.6 | 80.4 | 127.6 |
| VPCrO/γ-$Al_2O_3$ | 96.5 | 77.5 | 80.3 | 124.2 |

According to the above-mentioned reaction conditions, compared to the other promoter elements Co provides the best effects on the activity and selectivity behaviour of alumina supported VPO catalysts.

Example 5

Example 5 describes the activity and selectivity of VPO catalysts on a $TiO_2$ carrier used during an ammoxidation reaction carried out according to the invention.

5 g of catalyst, as described in examples 3 and 4, was loaded in the reactor along with the diluent corundum particles (1:1 by weight) and the reaction was performed under the following conditions. A reaction temperature of 350 to 400° C. was used, and the GHSV comprised between 650-750 h$^{-1}$. The contact time consisted of 4.8 to 5.5 seconds. The mole ratio of 2,6-DCT:$H_2O$:$NH_3$:air:$N_2$ was 1:15:3-4:21, the molar concentration of 2,6-DCT was 2.4% and the ratio of O/$NH_3$ was 1.1%. The results are depicted in Table 2.

TABLE 2

Influence of promoters on the activity and selectivity behaviour of TiO$_2$ supported VPO catalysts.

| Catalyst | Conversion, % (2,6-DCT) | Yield, % (2,6-DCBN) | Selectivity, % (2,6-DCBN) | STY (g/kg · cat/h) |
|---|---|---|---|---|
| VPCrO/TiO$_2$ | 97.1 | 83.9 | 86.4 | 134.5 |
| VPMoO/TiO$_2$ | 93.8 | 79.3 | 84.5 | 127.1 |
| VPCoO/TiO$_2$ | 91.8 | 78.5 | 85.5 | 125.8 |
| VPFeO/TiO$_2$ | 90.0 | 76.2 | 84.7 | 122.1 |

According to the above-mentioned reaction conditions, compared to the other promoter elements Cr provides the best effects on the activity and selectivity behaviour of VPO catalysts supported on TiO$_2$.

Example 6

Example 6 refers to the influence of water vapour in the feed gas on the catalytic performance of a VPCrO/TiO$_2$ (anatase) catalyst.

5 g VPCrO/TiO$_2$ (anatase) catalyst, as described in examples 3 and 4, was loaded in the reactor together with the diluent corundum particles (1:1 by weight) and tested the influence of water vapour in the feed gas on the catalytic performance of the catalyst. The reaction was performed under the following reaction conditions. A reaction temperature of 350 to 400° C. was used. The mole ratio of 2,6-DCT:NH$_3$:air was 1:4:21, the molar concentration of 2,6-DCT was 2.1 to 3.8%, and the ratio of O/NH$_3$ was 1.1%. The results are illustrated in Table 3.

TABLE 3

Influence of H$_2$O/2,6-DCT mole ratio on the activity and selectivity behaviour VPCrO/TiO$_2$ (anatase) catalyst.

| H$_2$O/2,6-DCT mole ratio | Conversion, % (2,6-DCT) | Yield, % (2,6-DCBN) | Selectivity, % (2,6-DCBN) | STY (g/kg · cat/h) |
|---|---|---|---|---|
| 0 | 86.0 | 76.0 | 88.4 | 121.8 |
| 7 | 92.6 | 80.6 | 87.0 | 129.2 |
| 15 | 97.1 | 83.9 | 86.4 | 134.5 |
| 25 | 96.8 | 80.8 | 83.5 | 129.5 |

In conclusion, the addition of water vapour in the feed gas has a beneficial effect on the catalytic performance of a VPCrO/TiO$_2$ catalyst, at a ratio of up to 25 moles water per each mole 2,6 DCT fed.

Example 7

Example 7 describes an ammoxidation reaction carried out following particular reaction conditions according to the invention and the catalytic performance of the used catalyst.

5 g VPO/TiO$_2$ (anatase) catalyst, as described in examples 3 and 4, was loaded in the reactor together with the diluent corundum particles (1:1 by weight) and the catalytical performance of the catalyst was tested under the following reaction conditions. A reaction temperature of 350 to 400° C. was used and the GHSV was 1495 h$^{-1}$. The contact time consisted of 2.4 seconds. The mole ratio of 2,6-DCT:H$_2$O:NH$_3$:air:N$_2$ was 1:20:3.0-4.5:23:30. The catalyst is observed to exhibit tremendous performance during time-on stream studies over period of 100 continuous hours under one set of conditions. The yield of 2,6-DCBN based on 2,6-DCT charged is found to be 81.0% at almost total conversion (100%) of 2,6-DCT, the space-time yield (STY) of 2,6-DCBN was 130 g/kg cat/h.

Example 8

Example 8 describes an ammoxidation reaction carried out following particular reaction conditions according to the invention and the catalytic performance of the bulk VPO catalyst with a P/V ratio of 0.7.

5 g of bulk VPO catalyst with a P/V ratio of 0.7 (atomic ratio), as described in examples 1 and 4 was loaded in the reactor along with the diluent particles (1:1 by weight, corundum particles) and the reaction was performed under the following conditions. A reaction temperature of 400 to 440° C. was used and the GHSV was 1295 h$^{-1}$. The contact time consisted of 2.86 seconds. The mole ratio 2,6-DCT:H$_2$O:NH$_3$:air was 1:15:6:50. Molar concentration of 2,6-DCT is 1.4%. The yield of 2,6-DCBN based on 2,6-DCT charged is found to be 75.6% at a conversion of 2,6-DCT of 95.0%. The space-time yield (STY) of 2,6-DCBN was 121 g/kg cat/h

Example 9

Example 9 describes an ammoxidation reaction carried out following particular reaction conditions according to the invention and the catalytic performance of the bulk VPO catalyst with a P/V ratio of 0.5.

5 g of bulk VPO catalyst with a P/V ratio of 0.5 (atomic ratio), as described in examples 1 and 4 was loaded in the reactor along with the diluent particles (1:1 by weight, corundum particles) and the reaction was performed under the following conditions. A reaction temperature of 400 to 440° C. was used and the GHSV was 1199 h$^{-1}$. The contact time consisted of 3.0 seconds. The mole ratio 2,6-DCT:H$_2$O:NH$_3$:air was 1:15:6:50. Molar concentration of 2,6-DCT is 1.4%. The yield of 2,6-DCBN based on 2,6-DCT charged is found to be 68.0% at a conversion of 2,6-DCT of 98.0%. The space-time yield (STY) of 2,6-DCBN was 109 g/kg cat/h.

Example 10

Example 10 describes an ammoxidation reaction carried out following particular reaction conditions according to the invention and the catalytic performance of the bulk VPO catalyst with a P/V ratio of 0.95.

5 g of bulk VPO catalyst with a P/V ratio of 0.95 (atomic ratio), as described in examples 1 and 4 was loaded in the reactor along with the diluent particles (1:1 by weight, corundum particles) and the reaction was performed under the following conditions. A reaction temperature of 400 to 440° C. was used and the GHSV was 1180 h$^{-1}$. The contact time consisted of 3.05 seconds. The mole ratio 2,6-DCT:H$_2$O:NH$_3$:air was 1:15:6:50. Molar concentration of 2,6-DCT is 1.4%. The yield of 2,6-DCBN based on 2,6-DCT charged is found to be 72.0% at a conversion of 2,6-DCT of 93.0%. The space-time yield (STY) of 2,6-DCBN was 115 g/kg cat/h.

Example 11

Example 11 describes an ammoxidation reaction carried out according to the invention.

The reaction was performed by the process described in example 4 using 5 g of VPO/TiO$_2$ (anatase) catalyst along with the diluent particles (1:1 by weight, corundum particles) at higher air/2,6-DCT mole ratio under the following conditions. A reaction temperature of 380 to 400° C. was used and the GHSV was 1056 h$^{-1}$. The contact time consisted of 3.4 seconds. The mole ratio 2,6-DCT:H$_2$O:NH$_3$:air was 1:15:4.6:35. Molar concentration of 2,6-DCT is 1.8%. The yield of 2,6-DCBN based on 2,6-DCT charged is found to be 76.2% at a conversion of 2,6-DCT of 99.7%. The space-time yield (STY) of 2,6-DCBN was 122 g/kg cat/h.

Example 12

Example 12 illustrates the influence of ethyl bromide in the presence or absence of water vapour added during an ammoxidation reaction according to the invention.

5 g of the following catalyst particles, as described in examples 3 and 4, were loaded in the reactor along with the diluent corundum particles (1:1 by weight) and tested the influence of addition of ethyl bromide (2% V/V) in presence and absence of water vapour. The reaction was performed under the following conditions. A reaction temperature of 350 to 400° C. was used. The mole ratio 2,6-DCT:H$_2$O:NH$_3$:airN$_2$ was 1:15:3-4:21:0-29. Molar concentration of 2,6-DCT is 1.4 to 3.8%. The results are summarised in Table 4.

TABLE 4

Influence of ethyl bromide in the presence or absence of water vapour on different VPO catalysts

| Catalyst | Conversion, % (2,6-DCT) | Yield, % (2,6-DCBN) | Selectivity, % (2,6-DCBN) | STY (g/kg · cat/h) |
|---|---|---|---|---|
| VPCoO/γ-Al$_2$O$_3$[a] | 99.3 | 89.5 | 90.1 | 141.5 |
| VPCoO/γ-Al$_2$O$_3$[b] | 99.5 | 83.2 | 83.6 | 131.5 |
| VPCrO/TiO$_2$[a] | 96.3 | 86.9 | 90.2 | 137.4 |
| VPCrO/TiO$_2$[b] | 96.3 | 87.6 | 91.0 | 138.5 |
| VPFeO/γ-Al$_2$O$_3$[a] | 98.3 | 86.6 | 88.1 | 136.9 |
| VPFeO/γ-Al$_2$O$_3$[b] | 99.2 | 80.6 | 81.3 | 127.5 |
| VPMoO/TiO$_2$[a] | 86.3 | 80.5 | 93.3 | 127.3 |
| VPMoO/TiO$_2$[b] | 95.1 | 86.8 | 91.3 | 137.2 |

[a] in absence of water vapour;
[b] in presence of water vapour

The addition of both water vapour and ethyl bromide admixture in the reactant feed gas has a detrimental effect especially on the catalytic performance of Co and Fe promoted catalysts. When adding ethyl bromide, in the absence of water vapour, both catalysts remarkably displayed a better catalytic performance exhibiting DCBN yields of 89.5% and 86.6% respectively. The addition of water vapour has no considerable effect in the presence of ethyl bromide in the reactant feed gas on the catalytic performance of the Cr promoted catalyst, while the addition of water vapour along with ethyl bromide has a positive effect on the catalytic performance of Mo promoted catalyst.

What is claimed is:

1. A method for the preparation of halogenated benzonitriles which comprises reacting halogenated C$_1$ to C$_6$ alkyl benzenes by vapor phase ammoxidation, in the presence of water vapor, at a reaction temperature in the range of 300 to 500° C., in the presence of a three-component catalyst into a fixed bed reactor wherein said catalyst consists of a promoted VPO active phase provided on a carrier.

2. The method according to claim 1, wherein said reaction temperature is in the range of 350 to 450° C.

3. The method according to claim 1, wherein the residence time of the halogenated C$_1$ to C$_6$ alkyl benzene in said reactor is less than 10 seconds.

4. The method according to claim 1, wherein said halogenated C$_1$ to C$_6$ alkyl benzene is di- or tri-halogenated C$_1$ to C$_6$ alkyl benzene.

5. The method according to claim 4, wherein said di- or tri-halogenated C$_1$ to C$_6$ alkyl benzene is di-halogenated toluene.

6. The method according to claim 5, wherein said di-halogenated toluene is 2,6-dichlorotoluene.

7. The method according to claim 1, wherein said catalyst is provided on an Al$_2$O$_3$ carrier.

8. The method according to claim 1, wherein said catalyst is provided on a TiO$_2$ carrier.

9. The method according to claim 8, wherein said TiO$_2$ carrier consists of the anatase phase.

10. The method according to claim 1, wherein said promoted VPO active phase provided on a carrier is a $V_1P_aM_bAl_cO_x$ or $V_1P_aM_bTi_cO_x$ catalyst wherein M is selected from the group consisting of Cr, Fe, Co and Mo; a is 0.1-2.0; b is 0.002-1.0; c is 2.0-10.0, and x is determined by the valences of other component elements.

11. The method according to claim 10, wherein M is Co or Cr.

12. The method according to claim 1, whereby the catalyst is diluted with an inert medium in the ratio of 0.5 to 2.0 by weight with respect to the weight of said catalyst prior to its addition to the reactor.

13. The method according to claim 12 wherein said inert medium comprises corundum particles, porcelain beads, quartz beads, and glass beads.

14. The method according to claim 1, comprising the step of supplying a halogenated alkane to said reactor.

15. The method according to claim 3, wherein the residence time of the halogenated C$_1$ to C$_6$ alkyl benzene in said reactor is less than 8 seconds.

16. The method according to claim 1, wherein about 7 to 40 moles of water per mole of C$_1$ to C$_6$ alkyl benzene are provided.

* * * * *

UNITED STATES PATENT AND TRADEMARK OFFICE
CERTIFICATE OF CORRECTION

| | | |
|---|---|---|
| PATENT NO. | : 7,576,233 B2 | Page 1 of 1 |
| APPLICATION NO. | : 10/516958 | |
| DATED | : August 18, 2009 | |
| INVENTOR(S) | : Martin et al. | |

It is certified that error appears in the above-identified patent and that said Letters Patent is hereby corrected as shown below:

Title Page, Item (75) Inventors, Line 4, "Van Deynse, Tessenderlo (BE);" should be changed to --Van Deynse, Koersel (BE);--

Column 6, Lines 17-18, "1-butyl-bromide," should be changed to --i-butyl-bromide,--

Column 6, Line 65, "whereby the after is" should be changed to --whereby the latter is--

Column 8, Line 1, "on an $Al_1O_3$ carrier," should be changed to --on an -$Al_2O_3$ carrier,--

Column 8, Line 6, "in addition, i" should be changed to --in addition, it--

Column 10, Line 2, "$(VO)_2P_2O$ phase" should be changed to --$(VO)_2P_2O_7$ phase--

Column 12, Line 41, Table 1, "(g/kg · cat/h)" should be changed to --(g/kg).cat/h)--

Column 13, Line 8, Table 2, "(g/kg · cat/h)" should be changed to --(g/kg).cat/h)--

Column 13, Line 41, Table 3, "(g/kg · cat/h)" should be changed to --(g/kg).cat/h)--

Column 14, Line 20, "121 g/kg cat/h" should be changed --121 g/kg cat/h.--

Column 15, Line 19, "2,6-DCT:$H_2O$:$NH_3$;air$N_2$" should be changed to --2,6-DCT:$H_2O$:$NH_3$;air:$N_2$--

Column 15, Line 29, Table 4, "(g/kg · cat/h)" should be changed to --(g/kg).cat/h)--

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO.      : 7,576,233 B2
APPLICATION NO. : 10/516958
DATED           : August 18, 2009
INVENTOR(S)     : Martin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1199 days.

Signed and Sealed this

Seventh Day of September, 2010

David J. Kappos
*Director of the United States Patent and Trademark Office*